United States Patent [19]

Arndt et al.

[11] Patent Number: 5,347,038
[45] Date of Patent: Sep. 13, 1994

[54] PROCESS OF THE PREPARATION OF 2,5-DI-PHENYLAMINO-TEREPHTHALIC ACID AND ITS DIALKYL ESTERS IN A HIGH PURITY

[75] Inventors: Otto Arndt, Hofheim am Taunus; Hermann Fuchs, Königstein/Taunus; Walter Gilb, Hofheim am Taunus, all of Fed. Rep. of Germany

[73] Assignee: Hoechst Aktiengesellschaft, Frankfurt am Main, Fed. Rep. of Germany

[21] Appl. No.: 64,116

[22] Filed: May 20, 1993

[30] Foreign Application Priority Data

Nov. 23, 1990 [DE] Fed. Rep. of Germany ....... 4037244
Jan. 16, 1991 [DE] Fed. Rep. of Germany ....... 4101084

[51] Int. Cl.$^5$ ............................................ C07C 229/00
[52] U.S. Cl. ........................................ 560/48; 562/457
[58] Field of Search ........................... 560/48; 562/457

[56] References Cited

U.S. PATENT DOCUMENTS 5,208,365  5/1993  Fuchs et al. ........................... 560/48

*Primary Examiner*—JoséG. Dees
*Assistant Examiner*—Samuel Barts

[57] ABSTRACT

An ecologically and economically improved process for the preparation of 2,5-di-phenylamino-terephthalic acid and its di-alkyl esters of the formula (1)

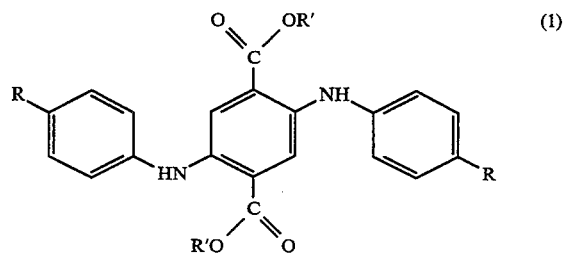

in which R is a hydrogen atom or a methyl group and R' is a hydrogen atom or a methyl or ethyl group.

11 Claims, No Drawings

PROCESS OF THE PREPARATION OF 2,5-DI-PHENYLAMINO-TEREPHTHALIC ACID AND ITS DIALKYL ESTERS IN A HIGH PURITY

The present invention relates to an ecologically and economically improved process for the preparation of 2,5-di-phenylamino-terephthalic acid and its di-alkyl esters, of the formula (1)

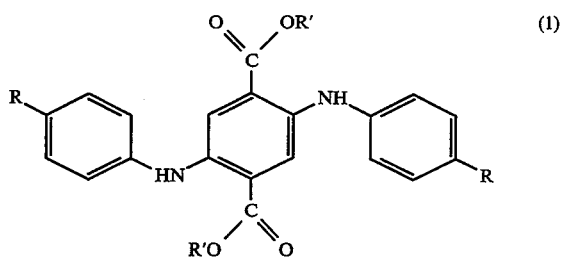

in which R is a hydrogen atom or a methyl group and R' is a hydrogen atom or a methyl or ethyl group.

It is known that 2,5-di-phenylamino-terephthalic acid and di-alkyl esters thereof can be prepared by a multi-stage process by cyclizing a succinic acid di-alkyl ester by a Dieckmann or double Claisen condensation to give the 2,5-dihydroxy-cyclohexadiene-1,4-dicarboxylic acid dialkyl ester (Fortschr. chem. Forschung, Volume 1 (1950) 685–724), subsequently converting this, by a condensation reaction with a primary phenylamine (for example aniline or toluidine) in xylene or ethylbenzene or in mixtures thereof in the presence of an aliphatic acid (for example acetic acid), into the 2,5-di-phenylamino-3,6-dihydro-terephthalic acid di-alkyl ester, dehydrogenating (oxidizing) this to give the 2,5-diphenylamino-terephthalic acid dialkyl ester, subsequently hydrolyzing this ester under alkaline conditions (for example in alcoholic sodium hydroxide solution) and liberating 2,5-di-phenylamino-terephthalic acid by treatment of the resulting 2,5-di-phenylamino-terephthalic acid di-sodium salt with an acid.

In the description of the preparation of di-phenylamino-terephthalic acid from a succinic acid ester by the route described above, a number of process parameters are reported in the literature (JP 49-108 036; DE-OS 1 915 436 and DE-OS 3 834 747 (EP 0 363 756)), such as, for example, solvents; intermediate isolation of some or all of the synthesis stage products (such as (1) succinylosuccinic acid di-alkyl ester; (2) 2,5-di-phenylamino-3,6-dihydro-terephthalic acid di-alkyl ester; (3) 2,5-di-phenylamino-terephthalic acid di-alkyl ester; (4) 2,5-di-phenylamino-terephthalic acid); the nature of the catalysts used, if appropriate with additives for the abovementioned intermediate stages (1), (2) and (3); the time sequence of the oxidation and hydrolysis (hydrolysis at the same time as oxidation or subsequently); dehydrogenating (oxidizing) agents (such as, for example, nitrobenzene and derivatives thereof, quinones, oxygen, iodine); working up of the auxiliaries used (such as, for example, solvents, phenylamine (aniline, p-toluidine), catalysts, additives).

The processes mentioned in the literature do not meet all the requirements of economy, low environmental pollution and quality of the end product at the same time.

Those processes which use nitroaromatics (for example nitrobenzene and derivatives such as nitrobenzene-m-sulfonic acid) instead of air or oxygen as the oxidizing agent for the dehydrogenation stage prove to be not particularly appropriate from the ecological standpoint.

A substance such as, for example, nitrobenzene should be used as a "synthetic constituent" in syntheses, but not as an auxiliary, since its secondary products such as, for example, aniline and azo- and azoxybenzene, must, be removed by expensive methods and at the same time can no longer be re-used because of heavy contamination. They would pollute the environment (waste water, landfill).

The use of oxygen gives only water as a secondary product if certain prerequisites are observed.

Those processes which use air with additives of the type of quinones and their derivatives (sulfonic acids, chloranil) or quaternary ammonium salts (DE-AS 1,144,285, EP 57873; EP 363 756) are also to be rejected for the same reasons, since these additives generally enter the waste water and moreover in some cases are a severe hazard to water. No single case of recovery of such additives is reported in the literature references which describe processes using them.

The use of only a single solvent for all the synthesis stages is advantageous.

The use of aniline, glacial acetic acid or dipolar aprotic solvents is a disadvantage, since these solvents are not suitable for all the synthesis stages, for example (a) aniline and glacial acetic acid are unsuitable for synthesis stage (1), and (b) N-methylpyrrolidone (NMP) is unsuitable for synthesis stage (4).

N-Methylpyrrolidone has indeed been employed for synthesis stages (1)–(4) in some processes. However, it is known that N-methylpyrrolidone is sensitive to alkali in an aqueous alkaline mixture (pH > 11.5, NMP Handbook, GAF Corp. 1972, page 102). No comment has been made in the literature mentioned on the yield of recyclable NMP (DE-B 1 082 907, JP 52-005739, JP 60-092245, Org. Prep. Proced. Int. 4 (1) 1972, 1).

Aromatics, preferably xylene, and occasionally also methanol are preferred in the processes described in the literature.

Xylene with noteworthy amounts of a second solvent component (for example dimethyl sulfoxide, see JP 52-059 135) is used for synthesis stage (1) in some processes. This second component is in general removed together with the salt content from synthesis stage (1) (for example sodium sulfate) before entry into synthesis stage (2) and passes into the waste water.

Only those processes which use xylene by itself, as described, for example, in JP 49-108 036 and DE-OS 1 915 436, are therefore recommended.

The two processes of the two literature references cited above have the common feature of the use of an isolated intermediate stage and the use of air (not 100% oxygen).

The process of JP 49-108 036 starts from the isolated product of synthesis stage (2). The process of DE-OS 1 915 436 starts from the isolated product of synthesis stage (1).

Neither process includes synthesis stage (1).

A.) Intermediate isolation of the product from synthesis stage (1):

A process without isolation of the intermediates stages is in principle more economical than a process in which one or more intermediate isolations are carried out. However, this only applies if the quality of the end product corresponds to the specified quality of High-Chem product.

In the case of a process which proceeds via several synthesis stages, it is appropriate for secondary components already obtained in the first stage to be removed as soon as possible, that is to say preferably even before entry into the second stage.

If the succinoylsuccinic acid dimethyl ester (product of synthesis stage (1)) is prepared in xylene by one of the processes of the literature references described and is isolated by steam distillation of the xylene, it is obtained in a good quality. However, the waste water from the steam distillation (="mother liquor") has a poor biological degradability.

If this pollution of waste water by components of poor biological degradability is to be avoided and the "purifying" intermediate isolation is dispensed with, a solution of the product of stage (1) in xylene contaminated with these components is obtained above 85° C. These secondary components result in a significant additional requirement of phenylamine, for example aniline or p-toluidine, in synthesis stage (2), which means that the content of secondary components in synthesis stage (3) which are not water-soluble is also increased significantly. In this case, intermediate isolation of the product from synthesis stage (2) could be appropriate. However, since noteworthy secondary components are additionally formed in the subsequent synthesis stage (3) too by the action of oxygen, the product from synthesis stage (3) must also be subjected to intermediate isolation.

B.) Intermediate isolation of the product of synthesis stage (3) for the purpose of purification:

It has been found, surprisingly, that after the steam distillation of the xylene, filtration of the di-phenylamino-terephthalic acid di-alkyl ester and hot washing with water, all the impurities in the material on the suction filter can be removed all at once by subsequently blowing out the di-ester on the suction filter with steam and washing it with methanol (Examples 1a, 15, 16). The impurities which can be washed out with methanol are mainly components of poor biological degradability. They can be disposed of by combustion. The aqueous mother liquor has a virtually 100% biological degradability (=COD elimination).

It is surprising here that hot washing with water by itself is not sufficient, for example, for a highly odoriferous content of impurities to be washed out from the material on the suction filter. This is achieved only after blowing out with steam. The product is then odorless.

The washing, described in JP 52-059 135, of the xylene reaction solution of stage (1) with aqueous sodium bicarbonate solution corresponds to the concept of already removing the impurities in stage (1). Laboratory experiments in this respect have shown, however, that the yield in stage (3) was considerably lower and the amount by weight of secondary components which can be isolated by extraction of the product from stage (3) with methanol did not decrease (cf. Examples 12 and 13).

In contrast, the shift in the purification stage to the product of stage (3) proves to be an effective purification method. The "prejudice" given by the prior art (JP 52 059 135) of purification of the reaction mixture of the product of stage (1) is thus overcome.

All the processes in which dehydrogenation (oxidation) and hydrolysis are carried out simultaneously, i.e. in which the product phase of synthesis stage (3) is passed through only briefly, if at all, and the product is not isolated until process stage (4), include entrainment of secondary components from the individual synthesis stages up to the end product.

It is thus surprising that the most effective purification possibility lies in washing the product of synthesis stage (3), i.e. at the synthesis stage at which the carboxylic acids are present as esters, especially since in the subsequent hydrolysis to give an aqueous solution of the di-sodium salt of synthesis stage (4), the clarification via active charcoal, which is possible per se, is not adequate if intermediate isolation of the product of synthesis stage (1) is omitted. DE-OS 38 34 747, Example 4, describes clarification of the alkaline ethanolic-aqueous reaction solution (pH 12.1) of the di-sodium salt. However, the clarification serves only to remove a very small amount of suspended substance. The main amount of the secondary components remains in the solution (for example the total excess of the phenylamine, for example p-toluidine, and the 2,5-di-p-toluidino-benzoic acid), and can therefore have an adverse influence on the quality of the free acid during its precipitation.

It was not foreseeable that, in a series of possible successive intermediate stages, precisely the intermediate stage of the di-phenylamino-terephthalic acid di-alkyl ester allows the most effective purification. It was also not foreseeable that after an ineffective hot washing with water, only blowing out with steam would lead to an odorless di-phenylamino-terephthalic acid di-alkyl ester.

The process described in the present specification comprises an appropriate allocation of the secondary components to the disposal possibilities, such as combustion of production residues and biological purification of the waste water, which surprisingly arose from the fact that the components of poor biological degradability can be passed for combustion, but those of good biological degradability pass into the waste water (in contrast to, for example, EP 363 756).

C.) Acid in synthesis stage (2):

It has been found that the use of organic acid in synthesis stage (2) (DE-OS 19 15 436) can be reduced considerably if the higher-boiling propionic acid, which boils at almost the same point as xylene, is used, because the discharge of organic acid associated with the azeotropic discharge of the water of reaction is considerably reduced in this way. It has furthermore been found that although propionic acid must also still be employed in amounts which are significantly higher (100 mol %) than the amount which is usually customary in the case of catalysts, the majority of the propionic acid can be recycled (the loss due to formation of propionic acid anilide or p-toluidide is low).

Although hexafluoropropanesulfonic acid reacts neither with aniline nor p-toluidine to give the sulfonic acid amide nor with xylene to give the sulfone and is already particularly suitable for synthesis stage (2) in a catalytic amount (<100 mol %), it has a poor biological degradability in the waste water (Example 17).

D.) Use of pure oxygen in a closed apparatus:

The combination of xylene/atmospheric oxygen was described for synthesis stage (3) (dehydrogenation (oxidation)) in JP 49-108 036 and DE-OS 19 15 436.

As is also the case with the other processes (for example methanol/air; DE-OS 38 34 747), the use of air means that the reaction must be carried out in an open apparatus, since the nitrogen content of the air blown in must be removed as a stream of waste gas, and therefore also the solvent vapors corresponding to the particular partial pressure, which must be removed from the stream of waste gas in an industrially expensive manner (cooling plant, washing tower) and must thus also be reduced to the legally prescribed values. This is expensive in terms of costly and uneconomical.

We have now found that this disadvantage can be avoided by metering 100% oxygen into the reaction vessel, and in particular preferably into the reaction mixture, below its surface. Since no waste gas is formed, the apparatus can remain closed. The reaction is carried out under normal or a slightly increased pressure of up to about 3 bar (cf. Examples 9–11, 18).

It has now furthermore been found that oxygen in the ratio to nitrogen present in the form of air (21% by volume of $O_2$, 78% by volume of $N_2$) and under the conditions described in the literature attacks the solvent xylene to a small extent to form essentially oxidation products of xylene.

The total amount of oxidation products of xylene and the number of these components is surprisingly not increased if 100% oxygen is used, in comparison with the use of air (about 0.1% by weight, based on the xylene).

Another advantage of the use of 100% oxygen in comparison with air is the possibility of limiting the oxygen content in the atmosphere above the reaction mixture to a value which is below the explosion range of the xylene/$N_2$/$O_2$ system, i.e. below about 9% by volume. The oxygen is metered in at the rate required by the current oxygen demand, a constant oxygen concentration being maintained in the gas space above the reaction mixture.

The rate of metering in is controlled via measurement of the oxygen concentration in the gas space above the reaction mixture (cf. Example 18).

Another advantage of the use of 100% oxygen in comparison with air is that the amount of gas blown in through the gas inlet pipe (immersed pipe) is only one fifth of that of air, corresponding to the content of about 21% by volume of oxygen in air.

In the case of air, the high flow of gas through the immersed pipe leads to evaporation of solvent and therefore to the formation of a solid plug which rapidly blocks the end of the immersed pipe, even if the end of the immersed pipe is widened like a bell. Because the stream of gas is reduced to one fifth, blocking no longer occurs when 100% oxygen is blown in.

Another advantage of the use of "100% oxygen" in comparison with air is that for the same volume flow, based on the oxygen, the reaction time for the oxidation of the product of synthesis stage (2) is shorter than if air is blown in (cf. Examples 9 and 10).

E.) Use of catalysts:

It has furthermore been found that the reaction of the product of synthesis stage (2) with the oxygen proceeds linearly with respect to time in a first time phase up to a conversion of about 50% (about 4–5 hours in the case of air or about 1–3 hours in the case of 100% $O_2$), as long as the product mentioned was still present as a sediment in a sufficient amount. This is then followed by an irregularity as the 2nd phase, which manifests itself in a slowing down of the conversion. Finally, in the 3rd and last phase, conversion proceeds in an accelerated manner until the reaction has ended (about 8–9 hours in the case of air or about 6–7 hours in the case of 100% $O_2$).

The metering of oxygen must be controlled precisely, especially in the 2nd and 3rd phase, to prevent the $O_2$ content in the gas space above the reaction mixture rising to more than 8% by volume and thus reaching the explosion range for the xylene/$N_2$/$O_2$ system. A speedier course of the conversion in the 2nd phase would thus be of advantage.

In a large number of laboratory experiments in stirred glass flasks, a slight positive effect in respect of smoothing of the conversion curves was found if V4A steel is present (as a gauze wound around the stirrer) (Example 3). This effect was improved after addition of a mixture of molybdenum powder and molybdenum(VI) oxide, but especially on addition of samarium(III) oxide or vanadium(IV) oxide acetylacetonate (Examples 1b, 6–8, 10). As a result of the speedier and more uniform course of the conversion, it is easier to maintain a constant $O_2$ concentration in the gas space above the reaction mixture, and the risk of entering the explosion range is therefore also smaller. The action of the catalyst manifests itself in an increase in the process reliability.

Another action of the catalysts was also found: the content of substances which are no longer biologically degradable in the waste waters of synthesis stage (3) is, surprisingly, reduced considerably (Examples 1a/2, 9/11).

2,5-Di-phenylamino-terephthalic acid is obtained in good yields and a high purity in a process aimed at ecological advance by the process according to the invention. It is suitable as a starting substance for the preparation of quinacridone pigments.

The present invention thus relates to an improved process for the preparation of 2,5-di-phenylamino-terephthalic acid and its di-alkyl esters, of the general formula (1)

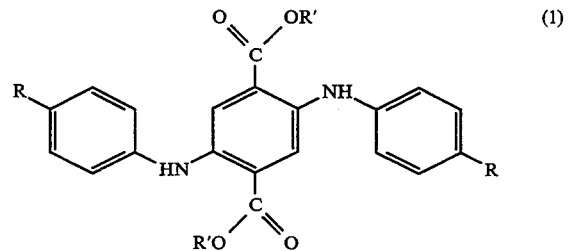

in which R is a hydrogen atom or a methyl group R' is a hydrogen atom or a methyl or ethyl group, by (1) reaction of a succinic acid di-alkyl($C_1$–$C_2$) ester by a Dieckmann condensation with a sodium alcoholate in xylene to give the di-sodium salt of the 2,5-dihydroxy-cyclohexadiene-1,4-dicarboxylic acid dialkyl($C_1$–$C_2$) ester, (2) reaction of the condensation product thus obtained, after decomposition of the di-sodium salt with an acid, with a phenylamine of the formula (2)

in which R has the abovementioned meaning, in the presence of an organic acid in xylene to give the 2,5-di-phenylamino-3,6-dihydroterephthalic acid di-alkyl($C_1$–$C_2$) ester, (3) dehydrogenation (oxidation) of the resulting 1,4-cyclohexadiene derivative with oxygen to give the corresponding 2,5-di-phenylamino-terephthalic acid di-alkyl($C_1$–$C_2$) ester, (4) hydrolysis of the resulting dialkyl ester in methanolic sodium hydroxide solution to give the corresponding 2,5-di-phenylamino-terephthalic acid di-sodium salt and (5) liberation of the 2,5-di-phenylamino-terepthalic acid from said di-sodium salt with an acid, in which the 2,5-dihydroxy-cyclohexadiene-1,4-dicarboxylic acid di-alkyl($C_1$–$C_2$) ester obtained in stage (1) is not isolated from its reaction mixture in xylene, propionic acid or hexafluoropropanesulfonic acid is used as the acid catalyst for the reaction with the phenylamine of the said formula (2) in stage (2), the dehydrogenation (oxidation) of the resulting 2,5-di-phenylamino-3,6-dihydro-terephthalic acid di-alkyl($C_1$–$C_2$) ester in stage (3) is carried out with 100% pure oxygen in a closed apparatus in the presence of a catalyst of V4A steel and/or of a transition metal of the periodic table of the elements, such as, for example, molybdenum or vanadium, and/or of a rare earth metal with variable oxidation levels, such as, for example, samarium or compounds thereof, such as, for example, samarium(III) oxide, or mixtures thereof, the oxygen content of the gas atmosphere above the reaction mixture being kept constant at below 8 percent by volume, the resulting 2,5-di-phenylamino-terephthalic acid di-alkyl($C_1$–$C_2$) ester is intermediately isolated from its aqueous medium by filtration, for example by filtration in a suction filter, and the di-alkyl($C_1$–$C_2$) ester intermediately isolated is subsequently purified by blowing out with steam on the suction filter and subsequently washing with methanol or ethanol, preferably methanol.

The process according to the invention is illustrated in more detail by the following examples, without being limited thereto.

EXAMPLE 1a 173 parts of a mixture of 149 parts of recycled xylene and 24 parts of propionic acid, and additionally 61 parts of propionic acid are added to 760 parts of a 15% strength xylene solution (reaction mixture), corresponding to 114 parts of 2,5-dihydroxy-cyclohexadiene-1,4-dicarboxylic acid dimethyl ester ("SucEst") (prepared under conditions as described, for example, in JP 52-059 135, but without addition of a second solvent component) in a glass apparatus with a tightly sealing stirrer, water separator and reflux condenser. 135 parts of p-toluidine are then allowed to run in as a melt at 75° C. under an inert gas atmosphere (nitrogen). Reaction to give 2,5-di-p-toluidino-3,6-dihydro-terephthalic acid dimethyl ester is completed by slowly increasing the temperature of the reaction mixture to about 103° C. in the course of about 3 hours. The water of reaction formed is condensed out via a condenser by pumping the nitrogen atmosphere in circulation (about 2 hours).

0.1–0.8 part of molybdenum or vanadium(IV) oxide acetyl-acetonate is then added as a catalyst, or a V4A wire gauze is wound around the stirrer. A stream of air, preheated if appropriate, of about 15 liters per hour is then introduced through an immersed tube at a temperature of 103° C. for about 8–9 hours. The stream of waste gas is passed over a separator for the water of reaction, over a cooler and over a washing column, for example with polyethylene glycol dimethyl ether, for absorption of xylene emissions. The current concentration of the oxygen is measured in the stream of waste gas. It is about 15% by volume on average. In this apparatus arrangement, the oxygen content of the air is utilized to the extent of about 25%. Samples are taken hourly for liquid chromatography (HPLC), and a conversion curve, expressed in percent by weight, of starting material and product is thus plotted. The 1st derivation (angle of the tangents) should decrease constantly from about 50% of the conversion. About 20% of the xylene (149 parts with 24 parts of propionic acid) is then distilled off. The remaining majority of the xylene is then distilled off by steam distillation, an aqueous suspension of 2,5-di-p-toluidino-terephthalic acid dimethyl ester finally being obtained. The xylene removed by steam distillation is purified and used for the preparation of the SucEst. The 2,5-di-p-toluidino-terephthalic acid dimethyl ester is isolated by filtration over a heated pressure suction filter (preferably fitted with a stirrer). The crystal-line crude product (226 parts by weight, melting point 205°–207° C.) on the suction filter is blown out with steam until it is odorless. It is then washed with methanol. 195 parts of methanol-moist 2,5-di-p-toluidino-terephthalic acid dimethyl ester (=97% of theory, based on the SucEst,) of melting point 215°–220° C. are obtained.

A salt-free waste water with a biological degradation rate of virtually 100% (=COD elimination) is moreover obtained. About 20–25 parts of solid which still contains only little target product can be isolated from the methanol filtrate after alkaline hydrolysis.

The methanol-moist di-ester is hydrolyzed with 150 parts of 33% strength sodium hydroxide solution in a mixture of recycled methanol and water in a VA stirred autoclave at 106° C. to give the di-sodium salt. After being let down, the alkaline product solution (pH 12.5) runs over a clarification filter and is then freed from methanol by distillation. The virtually methanol-free product solution runs into a receiver, in which it is simultaneously combined with concentrated hydrochloric acid in a pH-controlled manner.

177 parts of 2,5-di-p-toluidino-terephthalic acid with a melting point of 310° C. are obtained. The purity is >99% (HPLC, titration). The yield is 98% of theory, based on di-phenylamino-terephthalic acid di-methyl ester. A waste water containing sodium chloride and having a high biological degradation rate is moreover obtained. The residual COD (chemical oxygen demand following biological purification) of the overall process is very low.

EXAMPLE 1b

The procedure is as described in Example 1a, but instead of 15 liters of air/hour, 3 liters of $O_2$/hour are passed through the reaction mixture and 12 liters of $N_2$/hour are passed over the reaction mixture. Samarium(III) oxide is furthermore used as the catalyst.

The oxidation time is only 1.5 hours to 50% conversion and only 5 hours to 100% conversion.

The first derivation of the conversion curve continues to decrease constantly, even after 1.5 hours.

EXAMPLE 2

The procedure is as described in Example 1a, but without addition of a catalyst.

The same yield of 2,5-di-p-toluidino-terephthalic acid dimethyl ester and the same amount of secondary components which can be extracted by methanol are obtained. The time taken for complete oxidation is increased by about 2 hours to about 11 hours. The 1st derivation of the conversion curve reaches a minimum after 50% of the conversion, and then rises again significantly towards the end. The quality of the 2,5-di-p-toluidino-terephthalic acid is somewhat poorer:

| Example | Purity (%) HPLC | Titration with TMAH[1] | Number of secondary components HPLC |
|---|---|---|---|
| 1a | 99.5 | 99.5 | 1 |
| 2 | 98.3 | 95.2 | 2 |

The organic content which is not biologically degradable (=residual COD) in the waste water of the 2,5-di-p-toluidino-terephthalic acid dimethyl ester is significantly higher:

| Example | Residual COD g of $O_2$/kg of ester |
|---|---|
| 1a | 0 |
| 2 | 17 |

[1]THAM = tetramethylammonium hydroxide

EXAMPLE 3

The procedure is as described in Example 2, but with the absence of V4A steel catalyst during synthesis stages (1), (2) and (3). The results are as in Example 2, with a slight further deterioration in the purity of the acid (HPLC=97.4%) and the residual COD (=23 g of $O_2$/kg of di-ester).

EXAMPLE 4

The procedure is as described in Example 1a, but with molybdenum(V) chloride as the catalyst (0.150 parts by weight). A 2,5-di-p-toluidino-terephthalic acid quality which is improved further compared with Example 1a is obtained:

| Example | Purity (%) HPLC | Titration with TMAH | Number of secondary components HPLC |
|---|---|---|---|
| 1a | 99.5 | 99.5 | 1 |
| 4 | 100.0 | 99.6 | 0 |

EXAMPLE 5

The procedure is as described in Example 1a, but the synthesis is started with 114 parts by weight of pure 2,5-dihydroxy-cyclohexadiene-1,4-dicarboxylic acid dimethyl ester and only 129 parts by weight of p-toluidine.

The same yield of ester and acid as in Example 1a (195 and 177 parts by weight respectively) is obtained, but a reduced amount of secondary components which can be extracted by methanol and a better quality of the di-phenylamino-terephthalic acid. A shorter oxidation time is furthermore required.

| Example | Oxidation time (hours) to a conversion of 50% | 100% | Secondary components which can be extracted by methanol (after alkaline hydrolysis) parts by weight | Acid Purity (%) HPLC | Number of secondary components HPLC |
|---|---|---|---|---|---|
| 1a | 5 | 9 | 21.5 | 99.5 | 1 |
| 5 | 2 | 6 | 7.4 | 100.0 | 0 |

EXAMPLES 6-8

The procedure is as described in Example 5, but with other catalysts or without catalysts during the oxidation:

| No. | Catalyst | Oxidation time, hours to conversion of 50% | 100% | Secondary components which can be extracted by methanol (parts by weight) | Acid Content HPLC % | Number of secondary components HPLC |
|---|---|---|---|---|---|---|
| 5 | Mo/MoO$_3$ | 2 | 6 | 7.4 | 100.0 | 0 |
| 6 | Vanadium[1] | 1.5 | 5 | 14.0 | 99.8 | 1 |
| 7 | MoCl$_5$ | 3 | 6 | 6.7 | 99.6 | 1 |
| 8 | no catalyst no V4A | 4 | 7 | 10.0 | 99.0 | 4 |

[1]vanadium (IV) oxide acetylacetonate

In Examples No. 5-7, the 1st derivation of the conversion curve continues to decrease constantly. In Example 8, the behavior is as described in Example 2.

EXAMPLES 9-11

The procedure is as described in Example 5, but instead of 15 liters of air/hour, 3 liters of $O_2$/hour are passed through the reaction mixture and 12 liters of $N_2$/hour are passed over the reaction mixture:

| Example | Oxidation with | Catalyst | Oxidation time (hours) to a conversion of 50% | 100% | Residual COD g of $O_2$/ kg of Est |
|---|---|---|---|---|---|
| 5 | Air | Mo/MoO$_3$ | 2 | 6 | — |
| 9 | 100% oxygen | " | 1.5 | 5 | 5 |
| 10 | " | Sm$_2$O$_3$ | 1 | 5 | — |
| 11 | " | no catalyst | 2.5 | 7 | 18 |

The shorter oxidation times in Examples 9 and 10 are clearly seen. The yields of di-ester and acid are as for Example 1a.

EXAMPLES 12 and 13

The procedure is as described in Example 1a, but with the following modifications:
1) The xylene reaction solution of 2,5-dihydroxycyclohexa-1,3-diene-1,4-dicarboxylic acid dimethyl ester (SucEst) is washed with 250 parts of a 10% aqueous, hot sodium bicarbonate solution (Example 12) or, alternatively, with 250 parts of hot water (Example 13).

2) The oxidation is carried out with 100% oxygen according to Examples 9–11.

The yields of 2,5-di-p-toluidino-terephthalic acid and its di-methyl ester drop significantly in the case of washing of the SucEst with bicarbonate. The secondary components which can be extracted from the ester with methanol have not been decreased:

| Example | Yield Parts by weight Ester | Acid | Secondary products (methanol extract) parts by weight | Oxidation time hours |
|---------|------|------|------|------|
| 1a | 195 | 177 | 21.5 | 9 |
| 12 | 180 | 163 | 17.0[1)] | 6 |
| 13 | 190 | 175 | 24.6 | 7 |

[1)]Particularly high content of 2,5-di-p-toluidino-benzoic acid methyl ester

EXAMPLE 14

The procedure is as described in Example 2, but only 129 parts of p-toluidine are employed. 191 parts of di-ester, 175 parts of acid and 25 parts of methanol extract are obtained. Instead of 5.5 parts of p-toluidine, no p-toluidine was recovered in the steam distillate of the xylene.

However, the oxidation time is somewhat shorter (only 8 hours instead of 11).

This experiment shows that 129 parts of p-toluidine represent the lower limit of the amount to be used (theoretical amount to be used 107 parts). The quality of the 2,5-di-p-toluidino-terephthalic acid is as in Example 2.

EXAMPLES 15 and 16

The procedure is as described in Example 8, but the 2,5-di-p-toluidino-terephthalic acid di-methyl ester is employed for the hydrolysis in Example 16 in the form obtained from the steam distillation of the xylene reaction mixture according to Example 1a (215 parts by weight, melting 205°–210° C.), i.e. without the successive purification steps, described in that example, of
(a) blowing out the di-ester on the filter element using steam
(b) extraction of the di-ester with methanol.

The alkaline hydrolysis solution is clarified hot via active charcoal powder.

186 parts of 2,5-di-p-toluidino-terephthalic acid of poor quality are obtained.

Alternatively, an experiment is carried out (Example 15) in which the purification step (a) of blowing out the ester on the filter element using steam was carried out.

179 parts of a quality which lies between the qualities of Example 8 and Example 16 are obtained.

| No. | Yield Crude ester Parts by weight | Acid | Purity (%) HPLC | Titration TMAH | Secondary components (HPLC) Amount % | Number |
|-----|------|------|------|------|------|------|
| 8 | 209 | 177.0 | 99.0 | 99.8 | 1.0 | 4 |
| 15 | 206 | 179.0 | 97.5 | 97.0 | 2.5 | 3 |
| 16 | 215 | 186.0 | 91.2 | 93.0 | 8.8 | 6 |

It can be seen that the main amount of the impurities contained in the 2,5-di-p-toluidino-terephthalic acid is removed by blowing out the di-ester using steam.

EXAMPLE 17

The procedure is as described in Example 5, but instead of the 85 parts of propionic acid, 58 parts of hexafluoropropanesulfonic acid ("HFPS") are added as an auxiliary for the condensation of the SucEst with p-toluidine.

In spite of complete condensation, only 177 parts of 2,5-di-p-toluidino-terephthalic acid dimethyl ester (after the methanol wash) are obtained, since the conversion of the dihydro ester during the oxidation was still not quantitative even after 14 hours (according to HPLC, 5% of theory of the di-hydro ester was still found). Crusts which evidently retained a proportion of the di-hydro ester and thus withdrew it from the oxidation by atmospheric oxygen were formed on the wall of the stirred flask. Even when the amount of HFPS used was decreased to about 20 parts, the oxidation time for the di-hydro ester was still greater than 8 hours.

EXAMPLE 18

The procedure is as described in Example 11, but with 300 times the batch size (corresponding to 34,200 parts of SucEst) in a closed V4A stirred vessel.

After the condensation to give the 2,5-di-p-toluidino-3,6-dihydro-terephthalic acid dimethyl ester and removal of the water of reaction from the circulation by pumping the nitrogen in circulation over condensers, 100% oxygen gas is blown in through an immersed pipe (about 3000 parts). The oxygen content in the atmosphere above the reaction mixture is kept constant at between 2 and 6% by volume. The metering rate of the oxygen blown in is adjusted to the current oxygen requirement by appropriate valve control. After a maximum of 14 hours and after about 3000 parts of oxygen have been blown in, the oxidation is complete.

The yield and quality of the 2,5-di-p-toluidino-terephthalic acid (53,100 parts) and its di-methyl ester (58,500 parts) corresponding to those of Example 1a.

EXAMPLE 19

By varying the amount of recycled xylene (obtained by distilling off a larger or smaller proportion of the xylene from the finished reaction mixture; the residual amount of xylene is regenerated by steam distillation, see Example 1a), the content of recycled propionic acid can be controlled, since it has almost the same boiling point as xylene.

The DOC and COD (1) in the mother liquor of the 2,5-di-p-toluidino-terephthalic acid dimethyl ester are thus also influenced, including the values for the aqueous phase during steam distillation of the xylene:

| Example No. | Recycled propionic acid, percentage content | Vacuum distillation of xylene | DOC kg/tonne of ester | COD kg/tonne of ester |
|---|---|---|---|---|
| 9 and 11 | 0 | no | 227 | 685 |
| 7 | 40 | yes[2)] | 156 | 485 |
| | | | 71 | 200 |

[1)]DOC = dissolved organic carbon COD = chemical oxygen consumption
[2)]content of distilled xylene = 30%

It can be seen from this that it may be advantageous for ecological and also economic reasons (COD causes costs) not to regenerate all the xylene by steam distillation.

EXAMPLE 20

The procedure is as in Example 5, but aniline is employed instead of p-toluidine.

The amounts used are:

| | |
|---|---|
| Succinoylsuccinic acid dimethyl ester (SucEst) | 114 parts |
| Aniline | 112 parts |
| Propionic acid | 90 parts |
| Xylene | 450 parts |

After formation of the product from synthesis stage 2 (3 hours at 90° C.), a stream of air of 15 liters/hour is passed through at 97° C. for 8 hours.

About 80% of the xylene with a propionic acid content of 73 parts (=80% of the amount used) is distilled off under a vacuum of about 250 mbar at a temperature of up to a maximum of 100° C. The residual amount of the xylene is recovered by steam distillation.

The product (di-ester) is isolated by filtration and washed with hot water.

The water-moist ester (188 parts of dry product, 47 parts of water, melting point =145°-162° C.) is washed with 239 parts of hot methanol and filtered hot.

175 parts of methanol-moist 2,5-di-anilino-terephthalic acid methyl ester =93% of theory, based on the SucEst, of melting point 160°-164° C. are obtained. A salt-free waste water having a high biological degradation rate (COD=100%) is also obtained.

About 4 parts of solid can be isolated from the methanol filtrate after alkaline hydrolysis. The methanol-moist ester is hydrolyzed, precipitated and isolated as described in Example 1a. 156 parts of 2,5-di-anilino-terephthalic acid are obtained.

The purity is ≧99% (HPLC, titration).

The yield is 96% of theory, based on the di-ester, or 90% of theory, based on the SucEst. A salt-containing waste water having a high biological degradation rate (COD elimination=93%) is also obtained.

EXAMPLE 21

The procedure is as in Example 20, but the crude, water-moist ester (188 parts of dry product) on the suction filter is not washed with methanol.

After hydrolysis, 164 parts of 2,5-di-anilino-terephthalic acid are obtained. The purity is 97-98% (HPLC, titration).

Quality comparison by HPLC (area %):

| Example No. | Main constituent | Number of secondary components |
|---|---|---|
| 20 | 98.6 | 2 |
| 21 | 97.2 | 4 |

The following comparison shows the influence of the secondary components which can be extracted with methanol on the waste water:

| Example No. | COD kg of $O_2$ | Residual COD kg of $O_2$ | DOC kg of C per tonne of acid |
|---|---|---|---|
| 20 | 206 | 15 | 116 |
| 21 | 250 | 36 | 125 |

Since the secondary components which can be extracted with methanol can be burnt, the methanol wash provides a considerable contribution to decontamination of the waste water.

EXAMPLE 22

The procedure is as in Example 20, but an apparatus for automatic process control is used.

Moreover, 0.54 part of vanadium(IV) oxide acetylacetonate is used as the catalyst for the oxidation (dehydrogenation). The oxidation time is only 6 hours, instead of 8. 183 parts of water-moist ester (melting point 145°-154° C.) are obtained. The water-moist ester is hydrolyzed, precipitated and isolated as described in Example 1a. 159 parts of 2,5-di-anilino-terephthalic acid are obtained. The purity is 98% (titration).

We claim:

1. A process for the preparation of 2,5-di-phenylamino-terephthalic acid or one of its di-alkyl esters, of the formula (1)

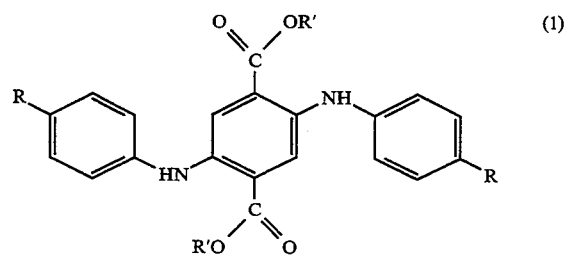

in which R is a hydrogen atom or a methyl group and R' is a hydrogen atom or a methyl or ethyl group, by (1) reaction of a succinic acid di-alkyl($C_1$–$C_2$) ester by a Dieckmann condensation with a sodium alcoholate in xylene to give the di-sodium salt of the 2,5-dihydroxy-cyclohexadiene-1,4-dicarboxylic acid dialkyl($C_1$–$C_2$) ester, (2) reaction of the condensation product thus obtained, after decomposition of the di-sodium salt with an acid, with a phenylamine of the formula (2)

in which R has the abovementioned meaning, in the presence of an organic acid in xylene to give the 2,5-di-phenylamino-3,6-dihydro-terephthalic acid di-alkyl($C_1$–$C_2$) ester, (3) dehydrogenation (oxidation) of the resulting 1,4-cyclohexadiene derivative with oxygen to give the corresponding 2,5-di-phenylamino-terephthalic acid di-alkyl($C_1$–$C_2$) ester, (4) hydrolysis of the resulting dialkyl ester in methanolic sodium hydroxide solution to give the corresponding 2,5-di-phenylamino-terephthalic acid di-sodium salt and (5) liberation of the 2,5-di-phenylamino-terephthalic acid from said di-sodium salt with an acid, which comprises not isolating the 2,5-dihydroxy-cyclohexadiene-1,4-dicarboxylic acid di-alkyl($C_1$–$C_2$) ester obtained in stage (1) from its reaction mixture in xylene, using propionic acid or hexafluoropropanesulfonic acid as the acid catalyst for the reaction with the phenylamine of said formula (2) in stage (2), carrying out the dehydrogenation (oxidation) of the resulting 2,5-diphenylamino-3,6-dihydro-terephthalic acid di-alkyl($C_1$–$C_2$) ester in stage (3) with 100% pure oxygen in a closed apparatus in the presence of a catalyst of V4A steel and/or of a transition metal of the periodic table of the elements and/or of a rare earth metal having variable oxidation levels or a compound thereof, or a mixture thereof, the oxygen content of the gas atmosphere above the reaction mixture being kept constant at below 8 percent by volume, intermediately isolating the resulting 2,5-di-phenylamino-terephthalic acid di-alkyl($C_1$–$C_2$) ester from the aqueous medium by filtration, and subsequently purifying the di-alkyl(-$C_1$–$C_2$) ester intermediately isolated by blowing out with steam on the suction filter and subsequently washing with methanol or ethanol.

2. The process as claimed in claim 1, wherein the dehydrogenation (oxidation) of the 2,5-di-phenylamino-3,6-dihydro-terephthalic acid di-alkyl($C_1$–$C_2$) ester is carried out in the presence of molybdenum, vanadium, samarium, $MoO_3$, $MoCl_5$, vanadium(IV) oxide-acetylacetonate or $Sm_2O_3$ or a mixture thereof as the catalyst.

3. A process for the preparation of 2,5-diarylamino-terephthalic acid or a di-salt or di-alkyl ester thereof, comprising:
  a. condensing succinic acid di-alkyl ester by Dieckmann condensation to form the intermediate product 2,5-dihydroxy-cyclohexadiene-1,4-dicarboxylic acid di-alkyl ester in a xylene-containing reaction medium;
  b. without isolating the intermediate product of said step a. from the xylene-containing reaction medium, reacting said intermediate product of said step a with an aromatic amine in the presence of propionic acid or hexafluoropropanesulfonic acid as an acid catalyst for this reaction to form the intermediate product 2,5-di-arylamino-3,6-dihydro-terephthalic acid di-alkyl ester;
  c. dehydrogenating the resulting intermediate product of said step b. in a reaction mixture in a closed reaction zone with essentially pure oxygen in the presence of a catalyst, said essentially pure oxygen being introduced below the surface of the reaction mixture, said closed reaction zone defining a gas atmosphere above the surface of the reaction mixture, which gas atmosphere is controlled in oxygen content to contain less than 8 percent oxygen by volume;
  d. intermediately isolating the resulting 2,5-di-arylamino-terephthalic acid di-alkyl ester from said reaction mixture in a filtration zone, as a crystalline crude product; subsequently purifying the thus-isolated crude crystalline product by blowing it with steam and subsequently washing the thus-blown crystalline product with methanol or ethanol.

4. The process as claimed in claim 3, wherein the acid catalyst in said step b. consists essentially of propionic acid.

5. The process as claimed in claim 3, wherein, due to the non-isolation of the product of said step a., the xylene-containing reaction medium present during said step a. is also essentially present during said step b., and the water of reaction formed during said step b. is removed such that the reaction medium for said step c. also comprises xylene; and the xylene present during said step c. is removed by steam distillation until an aqueous medium forms and the product of said step c. becomes suspended in said aqueous medium.

6. The process as claimed in claim 3, wherein, in said step d., the filtration zone comprises a heated pressure suction filter, and the crude crystalline product is blown with steam while on the suction filter until said product is essentially odorless.

7. The process as claimed in claim 3, wherein the isolated and purified product of said step d. is hydrolyzed to obtain the corresponding 2,5-di-arylamino-terephthalic acid.

8. The process as claimed in claim 7, wherein the isolated and purified product of said step d. is hydrolyzed with a sodium hydroxide solution to obtain the di-sodium salt of the 2,5-di-arylamino-terephthalic acid, and said corresponding acid is liberated from said di-sodium salt with an acid.

9. The process as claimed in claim 3, wherein said aromatic amine of said step b. is aniline or p-toluidine.

10. The process as claimed in claim 3, wherein said step c. is carried out in the presence of one or a mixture of the following metal catalysts: V4A steel, a transition metal of the periodic table of the elements, a rare earth metal having a variable oxidation level, or a compound or compounds of a said metal catalyst.

11. The process as claimed in claim 10, wherein said metal catalyst or compound or compounds thereof is molybdenum, vanadium, samarium, $MoO_3$, $MoCl_5$, vanadium(IV) oxide-acetylacetonate or $SM_2O_3$ or a mixture thereof.

* * * * *